United States Patent [19]

Chang

[11] 4,230,79[?]
[45] Oct. 28, 198[0]

[54] UNITIZED URIC ACID TEST COMPOSITION AND DEVICE

[75] Inventor: Eppie S. Chang, Elkhart, Ind.

[73] Assignee: Miles Laboratories, Inc., Elkhart, Ind.

[21] Appl. No.: 877,500

[22] Filed: Feb. 13, 1978

[51] Int. Cl.$^2$ ............................................. G01N 31/14
[52] U.S. Cl. ...................................... 435/10; 435/28; 435/191; 435/814
[58] Field of Search ................ 195/62, 66 R, 103.5 U, 195/99, 103.5 R; 435/10, 28, 191, 814

[56] References Cited

U.S. PATENT DOCUMENTS

| | | | |
|---|---|---|---|
| 3,616,231 | 10/1971 | Bergmeyer et al. | 195/66 R |
| 3,928,137 | 12/1975 | Monte et al. | 195/99 X |
| 4,062,731 | 12/1977 | Snoke et al. | 195/103.5 U |

OTHER PUBLICATIONS

Gochman et al., *Clinical Chemistry*, vol. 17, No. 12 (1971), pp. 1154–1159.

*Primary Examiner*—Esther M. Kepplinger

*Attorney, Agent, or Firm*—Charles J. Herron

[57] ABSTRACT

Unitary test means, such as a composition or devic[e] purified uricase for use therein, method of making th[e] test device and process for determination of uric aci[d] therewith are disclosed. More particularly, there i[s] provided in test means for the detection of uric aci[d] comprising a uricase-active substance, at least one chr[o]mogen, and a peroxidatively active substance, the im[-]provement wherein the uricase active substance is an[i]mal-originated uricase which is free of pH sensitiv[e] contaminants having a molecular weight of less tha[n] about 6000. The test means can take the form of a co[m]position which can further include at least one couplin[g] agent and at least one stabilizing agent. The compos[i]tions can optionally be incorporated with a carrier, suc[h] as a tablet or matrix, to provide a test device. The ur[i]case-active substance is purified by fractionation c[f] standard animal uricase preparations to remove lo[w] molecular weight contaminants and is stable over [a] heretofore unattainable pH range, permitting a unitize[d] test.

16 Claims, No Drawings

UNITIZED URIC ACID TEST COMPOSITION AND DEVICE

BACKGROUND OF THE INVENTION

The present invention relates generally to the field of diagnostic tests and, more particularly, to a unitary reagent test for determining uric acid in a fluid sample.

In primate metabolism, there is a constant endogenous conversion of ingested nucleoproteins to purines and pyrimidines. The purines, by a catabolic process, then undergo further deamination and partial oxidation to uric acid, which in man is normally excreted in the urine. Thus, a nominal concentration of uric acid is present in human blood and urine at all times.

Ingestion of purine-containing food normally has no affect on the uric acid blood serum content, except in the case of renal insufficiency, in which event the concentration is elevated. In certain other pathological conditions not associated with dietary ingestion of purine-containing food, for example uremia and gout, there is an abnormal increase in the amount of uric acid found in the blood serum. Also, uric acid concentration in the serum is elevated in conditions associated with excessive destruction of leucocyte nuclei, such as leukemia and pneumonia.

A serum uric acid test has been recognized as useful as an aid in diagnosing the foregoing conditions and, in some instances, distinguishing between closely related abnormal conditions, for example, gout and arthritis. Gout is characterized by an abnormal increase in blood serum uric acid, whereas arthritis does not exhibit such increase. It is therefore desirable to provide a simple and economical test which affords a precise and specific determination of the concentration of uric acid in blood serum.

Uric acid is normally found in blood serum in quantities from about 0.7 to about 6.0 milligrams per 100 ml of blood serum, generally reported as milligrams percent (mg%). In the abnormal conditions enumerated above, the uric acid content in the blood serum often attains values of 10 mg% or higher.

The prior art has disclosed a number of methods for determining uric acid in blood serum. Among the more widely used conventional methods are colorimetric procedures utilizing blood filtrates. Some of these procedures depend upon the precipitation of uric acid from the blood filtrate, for example, as a silver salt, and the formation therewith of a chromogenic adduct by reaction with either a phosphotungstate or arsenotungstate. Other methods utilizing the blood filtrate depend upon the direct treatment of the filtrate with a tungstic acid in the presence of a cyanide-urea solution to develop a color which is then measured using conventional techniques for quantitative estimation of uric acid concentration.

More recently, methods have been proposed which involve the catalyzed oxidation of uric acid to allantoin and hydrogen peroxide. This oxidation is usually accomplished in the presence of atmospheric oxygen and utilizes a material having uricase activity, the reaction occurring at or near pH 9. In such methods a spectrophotometer can be employed to measure the disappearance of the characteristic uric acid spectrum during its conversion to allantoin and hydrogen peroxide. Another method utilizes a colorimetric means for measuring the hydrogen peroxide produced in stoichiometric amounts during such degradation of uric acid. See, for example, Albaum U.S. Pat. No. 3,349,006 and Wachte U.S. Pat. No. 3,335,069 (both assigned to the assignee of the present invention).

In the enzymatic conversion test, where the amount of hydrogen peroxide produced is directly proportional to the amount of uric acid present in the blood serum the hydrogen peroxide is detected by means of a color change produced upon oxidation of a color forming substance in the presence of a substance having peroxidative activity. This reaction occurs at acid pH. A catalase inhibitor, such as sodium azide or sodium cyanide, has usually been required to prevent catalase destruction of the peroxide. The color obtained is then compared visually to standards, or measured electronically, to give a quantitative estimation of uric acid present in the fluid being tested.

French Pat. No. 72/31557 discloses a fundamentally different enzyme catalyzed reaction wherein catalase and aldehyde-free methanol are added along with the uricase to the sample (buffered to pH 8), and 3-methyl 2-benzothiazolinone hydrazone (buffered to pH 3) and FeCl$_3$ in HCl are then added to give a blue coloration Kano U.S. Pat. No. 3,862,885 discloses a process for uric acid determination by generating hydrogen peroxide with a microbe-originated uricase and a catalase inhibitor (buffered to pH 5.5–7.0) and measuring the peroxide generated in the presence of an anionic surface active agent, a chromogen and peroxidase (pH 4.0–7.0)

Gochman and Schmitz have reported using 3-methyl 2-benzothiazolinone hydrazone hydrochloride with N,N-dimethylaniline to form an azo dye indicator in automated determinations of uric acid, *Clin. Chem* 17 1154 (1971).

Notwithstanding the contributions by prior workers in the field, these procedures have had the disadvantage of requiring a series of separate operations, usually carried out in liquid phase. Coupled reactions using animal uricase and peroxidase simultaneously have been considered impossible because of the competition between uric acid and the chromogen, both being oxidized by H$_2$O$_2$ in the presence of peroxidase, and of the drastic difference in the optimum pH of the two enzymes used The prior art systems where both reactions are carried out at or near the same pH have the further drawback that certain reaction component candidates, such a animal-originated uricase, which exhibit superior performance characteristics cannot be used therein because they are inoperable as a component of the peroxidase generating system within the pH range required by th reaction.

Thus, incorporation of means for uric acid determination in a stabilized, unitary reagent test has heretofore been impossible.

OBJECTS OF THE INVENTION

It is therefore an object of the present invention to provide a unitized test means, such as a composition o device, for determination of uric acid in body fluids.

It is another object of the present invention to provide a uric acid test composition and device of a type which is particularly convenient for testing of large numbers of samples.

Another object of the invention is to provide a single operation uric acid test device which is stable over an extended time.

An additional object of the invention is to provide an improved test for the detection of uric acid wherein th re-identified advantages are achieved through in-
oration therein of a novel purified, animal-
inated, uricase-active substance, free of pH sensitive
aminants.

ther objects and a fuller understanding of the inven-
will be had by referring to the following descrip-
and claims drawn to preferred embodiments
eof.

SUMMARY OF THE INVENTION accordance with the present invention there are
ided unitary test means, such as a composition or
ce, purified uricase for use therein, method of mak-
he test device and process for determination of uric
therewith. More particularly, there is provided in
means for the detection of uric acid comprising a
ase-active substance, at least one chromogen, and a
xidatively active substance, the improvement
rein the uricase-active substance is animal-
inated uricase which is free of pH sensitive contami-
s having a molecular weight of less than about 6000.
test means can take the form of a composition
ch can further include at least one coupling agent
at least one stabilizing agent. The compositions can
onally be incorporated with a carrier, such as a
et or matrix, to provide a test device. The uricase-
ve substance is purified by fractionation of standard
al uricase preparations to remove low molecular
ght contaminants and is stable over a heretofore
tainable pH range, permitting a unitized test.

he purified, animal-originated, uricase-active sub-
ce, a critical component of the above described
position, is prepared by fractionation purification of
mercially available animal uricase preparations,
as are available from Miles Research Products,
s Laboratories, Inc., Elkhart, Indiana 46514. Con-
inants which are sensitive to variation in pH and are
elatively low molecular weight, less than about
, are removed. Surprisingly, by this seemingly sim-
purification process, the uricase-active substance
duced is made stable over a pH range of from about
to about 7.5, thus enabling the preparation of a unit-
, enzyme-catalyzed uric acid test composition hav-
a plurality of reaction systems functional under a
le set of reaction parameters.

nimal uricase is a cuproprotein (a conjugated metal-
otein), and the $Cu^{++}$ is believed to be a part of the
lytic site of the enzyme. The structure of the copper
taining moiety of the active site may be schemati-
y represented by the following:

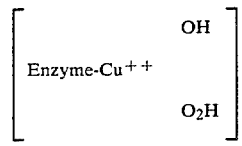

The cuproprotein nature of the enzyme causes it to be rapidly, but reversibly, inhibited by a variety of agents which are capable of simultaneous reduction of $Cu^{++}$ and complexation of $Cu^+$ ions. The uricase is therefore preferably purified by dialysis against a buffer with a low metal binding constant.

In a preferred embodiment, the enzyme is dialyzed against a solution containing buffers having a low metal binding constant, such as Tris (hydroxymethyl)-aminomethane (TRIS), piperazine-N,N'-bis (2-ethane-sulfonic acid (PIPES), N-tris-(hydroxymethyl) methyl-2-aminoethanesulfonic acid (TES) and phosphate buffer.

Uric acid is oxidized enzymatically by uricase to allantoin and hydrogen peroxide at about pH 7. The stoichiometry of the enzyme reaction proper, regardless of buffer or pH, is given by equation (1), i.e., the transfer of an electron pair from the urate monoanion to oxygen, yielding an unstable acid intermediate (1-carboxy-2,4,6,8-tetraazabicycl [3,3,0]-octa-4-en-3,7-dione), and hydrogen peroxide.

$$C_5N_4O_3H_3^- + O_2 + H_2O = C_5N_4O_4H_3^- + H_2O_2 \qquad (1)$$

The intermediate product is a stronger acid (lower pK) than uric acid [pK=4.5, versus pK=5.75 for urate; $pK_2$=11.5 versus $pK_2$=10.3 for urate] and is capable of stabilization by forming metal chelates with copper ($Cu^{++}$) and cobalt ($Co^{++}$). In the presence of a highly purified enzyme at pH 7.0, stoichiometric amounts of allantoin, hydrogen peroxide, and carbon dioxide are formed. The hydrogen peroxide is then reacted with the chromogens in the presence of peroxidase to give a red complex. The overall chemical reactions of the test are as follows:

$$\text{Uric Acid} + O_2 + H_2O \xrightarrow[\text{pH 7.0}]{\text{pH stable Uricase}} \text{Allantoin} + CO_2 + H_2O \qquad (2)$$

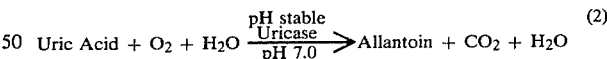

$$H_2O_2 + \text{3-alkyl-2-Benzothiazolinone Hydrazone} + \qquad (3)$$

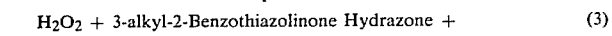

$$\text{coupling agent} \xrightarrow[\text{pH 7.0}]{\text{Peroxidase}} \text{Colored-Complex} + H_2O$$

In the present system the difficulties of competition between uric acid and the chromogen and of drastic difference in pH optimum of the enzymes are further overcome by employing a strong reducing agent, a hydrazone, and an extremely sensitive coupling agent which, in addition, serves as an activator of uricase. The chromgenic reactions using, for example, 3-methyl-2-benzothiazolinone hydrazone (MBTH) and primaquine diphosphate (PDP) are schematically represented in Diagram A as follows:

DIAGRAM A

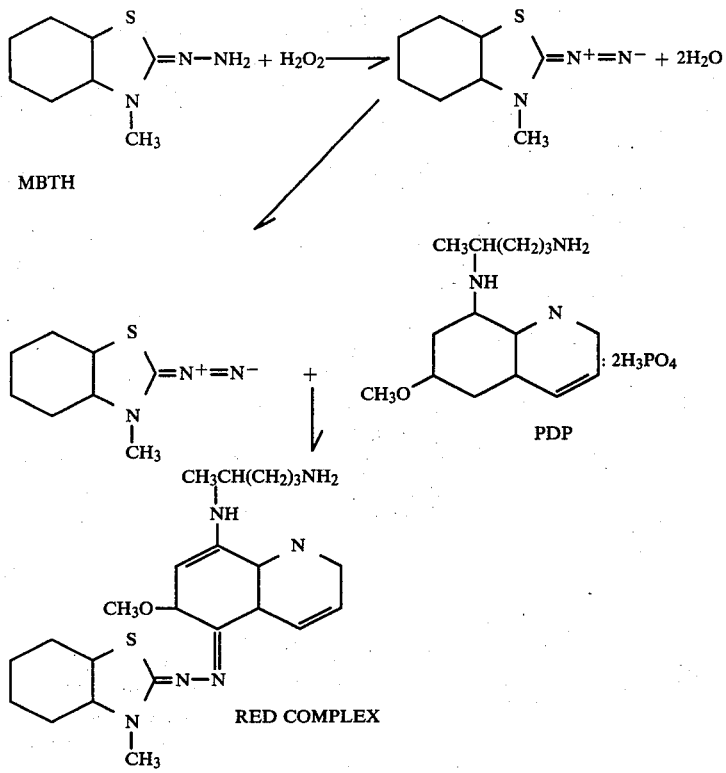

DESCRIPTION OF THE PREFERRED EMBODIMENTS

Although specific terms are used in the following description for the sake of clarity, these terms are intended to refer only to the particular embodiments of the invention selected for exemplary illustration, and are not intended to define or limit the scope of the invention.

The commercial uricase preparation is purified by a process which, in a preferred embodiment, comprises fractioning the uricase preparation to remove molecules having less than about 6,000 molecular weight. Such is done by various techniques including dialysis, column chromatography, gel sedimentation and the like.

The hydrazones are condensation products of a hydrazine with an aldehyde or ketone and contain the grouping C=NNH$_2$. Many hydrazones are capable of oxidatively coupling with certain aromatic amines or hydroxynapthalensulfonates to form a colored entity. Such include, among others, 3-methyl-2-benzothiazolinone hydrazone, 2-hydrazinobenzothiazole, N-methyl-pyridone-4-hydrazone, N-methyl-pyridone-2-hydrazone, N-methyl-quinolinone-2-hydrazone, methylquinolinone-4-hydrazone, N-methyl-2-benzothiazolinone hydrazone, N-methyl-thiazolinone-2-hydrazone, N-methyl-4-phenylthiazolinone-2-hydrazone, N-methyl-oxazolinone-2-hydrazone, N-methyl-benzoxazolinone-2-hydrazone and 1,3-dimethylbenzimidazolinone-2-hydrazone.

In a preferred embodiment of the composition, a 3-($C_1$-$C_4$ alkyl)-2-benzothiazolinone hydrazone chromogen, such as 3-methyl-2-benzothiazolinone hydrazone (MBTH), is used as the chromogen. Such hydrazones are strong reducing agents. The hydrazone is used in benzene solution at concentrations from a 0.05 mg% to about 0.2 mg%.

Exemplary of the coupling agents which can be in combination with the chromogenic hydrazone the following:

1. compounds having the general formula:

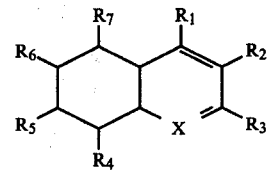

wherein X is C, N, or S; $R_1$ is H, OH, amino kylenediamine, or aminoalkanol or combines with where $R_2$ is H, to become NHCH$_2$CHOHCH$_2$; $R_2$ $R_3$ are the same or different and are H or SO$_3$H; $R_4$ OH, NHCH(CH$_3$) CH$_2$CH$_2$CH$_2$NH$_2$, or SO$_3$H; $R_5$ SO$_3$H or acetamino; $R_6$ is H or OCH$_3$; and $R_7$ is H, or NH$_2$; and the acid addition salts, such as the p phates, thereof.

2. compounds having the general formula R—2—R wherein each R is dimethylaniline, hydroxy nyl, benzothiazole, or benzophenone;

3. Thiamine or its acid addition salt;

4. methylphenylpropanediamine; and 5. phenothiazine.

Preferred coupling agents include primaquine phosphate (PDP), chromotropic acid, and 4, 4'-me lene bis (N,N' dimethylaniline)(MBDMA). The pling agent is used in aqueous solutions of from a 1.0 mg% to about 5.0 mg%.

composition can further include stabilizing carboxymethylcellulose (CMC) and polyox-
...ne ethers of fatty alcohols (BRIJ ® made by ICI States Inc., Wilmington, Del. 19897) being ad-
...eously selected. These are present in aqueous ...ns in total concentrations of from about 0.5 mg%
...t 5.0 mg%.
...lution containing composition according to the ...on can be used to detect uric acid by adding it to
fluid specimen such as urine. Formation of the ...phoric complex with resultant color change is
...d. However, the composition is more advanta-
...y used in the form of a solid preparation, rather ...a solution, and preferably in devices designed
...venience and reliability.
...n aspect of the invention, a device is prepared comprises an inert carrier and, incorporated
...ith, a composition according to the invention as ...ed above and illustrated in the examples. The
...rrier can take the form of a bibulous or non-bibu-
...rrier matrix or can be in a tablet or other conven-
...orm.
term carrier matrix refers to bibulous and non-
...s matrices which are insoluble in and maintain ructural integrity when exposed to physiological
...r liquids. Suitable bibulous matrices which can ...l include paper, cellulose, wood, synthetic resin
..., glass fiber, non-woven and woven fabrics and
... Non-bibulous matrices include organo-plastic ...ls like polypropylene. For convenience the ma-
... be associated with an insoluble support member
... one made of polystyrene.
rnatively, the inert carrier can be embodied in ...m of a pressed or molded tablet containing con-
...al carrier materials like disintegration agents, ...materials, and lubricants.
test device of the present invention demonstrates degree of stability, as shown in the examples.
ability can be even further improved by separat-
nponents of the composition on a substrate and ably packaging the finished product in foil, a
...nt containing container or the like. The physical ion of components can be accomplished by
..., by encapsulation of one or more component, of a separate matrix or substrate for different
nents, by placement of incompatible components osite sides of a substrate, or the like.
further aspect of the invention there is also pro-
... method for preparing a uric acid test device comprises impregnating, printing or otherwise
...ing an inert carrier with a composition of the ...on. If the carrier is impregnated with a composi-
liquid form, the carrier is then subjected to the drying.
invention further provides a method for using nposition or test device for the determination of
...id in a liquid sample. The sample is tested by ...ing the composition or device with the sample
serving any change in color. When a device of ...e having a bibulous carrier matrix is used, the
enters the matrix, and the color change is ob-
thereon. In addition to visual comparison, vari-
trumental methods can be employed to deter-
...y color change developed, thus increasing
...y of the test by obviating the subjective determi-
...of color by the human eye.
activity of the enzyme preparation is measured number of units of activity per milligram of dry weight. The Commission on Enzymes of the International Union of Biochemistry has defined an International Unit (I.U.) of enzyme activity as 1 micromole ($\mu$mol) of substrate utilized per minute under specified conditions of pH and temperature control.

The relationship between percent reflectance (%R), reported in the examples, and the concentration of the absorbing species (uric acid) is given by the Kubelka-Monk equation which is provided, along with a detailed discussion of reflectance spectrophotometry in Kortümi, G., *Reflectance Spectroscopy*, Springer-Verlag New York Inc., 1969. In the relationship defined by the Kubelka-Monk equation the %R value decreases as the uric acid concentration detected increases, and vice versa. Thus, the readings taken inversely correlate, according to the equation, with the concentration of uric acid detected. All readings were taken at 530 nanometers unless indicated otherwise.

Reflectance readings can be obtained from commercially available spectrophotometers such as Beckman DK-2 Spectrophotomer, Beckman Instruments, Inc., Fullerton, Calif. 92634 or Spectrocolorimeter SCF-1, Israel Electro-Optical Industry Ltd. (distributed in the U.S. by Broomer Research Corporation, Plainwell, Long Island, N.Y. 11803).

The examples shown are merely illustrative and are not to be construed as a limitation of the invention. One skilled in the art will be able to make such variations, substitutions and changes in the ingredients and parameters as may seem desirable.

EXAMPLE I

A purified, animal-originated, uricase-active substance of the invention was prepared as described below.

Five milliliters (ml) of uricase (Boehringer Mannheim GmbH, Mannheim, Federal Republic of Germany), activity 9 IU/ml, was enclosed in the dialysis bag formed of Spectrapor membrane (Spectrum Medical Industries, Los Angeles, Calif. 60916) which is permeable to molecules of less than 6,000 molecular weight. The uricase was dialyzed with stirring against 0.5 Molar (M) TRIS, at pH 7.0, for 18 hours at 4° Centigrade (C).

Studies were initiated to determine the minimum volume of buffer required for sufficient dialysis of the enzyme. One ml of uricase was dialyzed against 20 ml, 50 ml, 100 ml, and 1000 ml of buffer. The dialyzed uricases were all assayed, and the results indicated no significant difference in activities in the various buffer volumes (Table I).

TABLE I

| Activity of Uricase Dialyzed in Different Buffer Volumes | |
|---|---|
| Buffer Volume | Activity of Dialyzed Uricase I.U./ml |
| 20 ml | 6.5 |
| 50 ml | 6.2 |
| 100 ml | 6.4 |
| 1000 ml | 6.5 |

Thus, it appears from this that an end-point of substantial purity is reached for removal of contaminants even with the use of as little as 20 ml of buffer.

EXAMPLE II

Strips were prepared in a 2-dip process using uricase dialyzed against the various buffers indicated on Table II.

The first dip solution was formed by combining 0.5 ml uricase (3.0 I.U./ml), dialyzed against the respective indicated buffer, 0.5 ml of stabilizing agent (1.5 mg% CMC+0.8 mg% polyoxyethylene ether of aliphatic alcohol (BRIJ 35), 0.06 ml horseradish peroxidase, and 0.1 ml (3.75 mg%) of coupling agent PDP all in distilled water. The second dip solution was prepared by dissolving 5.0 milligrams (mg) of the chromogen MBTH in 10 ml of benzene.

Sheets of Whatman ET 31 filter paper (Whatman Inc., Clifton, N.J. 07014) 2.54 cm×10.16 cm in size were impregnated to saturation with the respective first dip solution, dried for 30 minutes at 50° C., saturated with the second dip solution, dried again, and cut to 5.1 mm×10.2 mm to provide devices of the invention.

The devices so prepared were then separated into three groups. Two of these groups were subjected to heat stress of 60° C. for periods of 24 and 72 hours, respectively. The third group was not subjected to heat stress at all (0) and served as a control.

These devices were then tested by delivering 0.03 ml aliquots thereof of serum samples containing the amounts of uric acid shown on Table II, and observing any resultant color change. Readings of %R were taken at 120 seconds with freshly prepared strips.

TABLE II

| | TIME (hours) | URIC ACID (mg %) | | | | |
|---|---|---|---|---|---|---|
| | | 2 | 4 | 6 | 8 | 10 |
| TRIS | 0 | 38.6 | 30.7 | 28.9 | 23.0 | 25.0 |
| | 24 | 44.8 | 35.6 | 30.0 | 30.0 | 26.3 |
| | 72 | 43.4 | 40.1 | 34.7 | 32.3 | 27.9 |
| PIPES | 0 | 39.0 | 33.7 | 31.1 | 28.5 | 26.5 |
| | 24 | 38.1 | 34.5 | 30.3 | 27.2 | 24.4 |
| | 72 | 35.4 | 35.6 | 31.0 | 29.2 | 28.8 |
| TES | 0 | 33.8 | 31.2 | 29.1 | 25.7 | 25.6 |
| | 24 | 34.3 | 31.0 | 28.5 | 27.1 | 24.2 |
| | 72 | 33.2 | 35.0 | 29.1 | 26.6 | 26.3 |

The results in Table II show an incremental decrease in percent reflectance (%R) as the uric acid concentration increases, the relationship being defined by the Kubelka-Monk equation. This indicates that each of the buffers tested is advantageously useful in preparing the purified, uricase-active substance.

EXAMPLE III

The effect on ultimate test sensitivity of pH variation of the dialysis buffer was examined.

Devices were prepared as in Example II, with the uricase having been dialyzed against phosphate buffer adjusted to the various pH levels shown in Table III. The data obtained, reported in %R, is set forth in Table III.

TABLE III

| pH | URIC ACID (mg %) | | | | |
|---|---|---|---|---|---|
| | 2.0 | 4.0 | 6.0 | 8.0 | 10.0 |
| 6.8 | 19.4 | 13.8 | 12.4 | 10.7 | 9.3 |
| 7.0 | 19.5 | 14.3 | 11.5 | 10.2 | 9.2 |
| 7.5 | 19.0 | 13.5 | 8.1 | 10.3 | 9.2 |

The results show an incremental decline with the increase of uric acid concentration. This indicates that uricase dialyzed in buffer having a pH from at least about pH 6.8 to at least about pH 7.5 gave high sensitivity in detection of uric acid.

Results obtained using uricase dialyzed against TRIS PIPES and TES buffers indicate a pH stability of th uricase over the same range.

EXAMPLE IV

Devices were prepared according to the followin procedure in which the coupling agents shown in Tabl IV were used instead of PDP.

MBTH, 0.2 gram (g), was dissolved in a mixture of 5 ml methanol and 10 ml H$_2$O. To 6 ml of this MBTI solution there was added 0.02 g of the selected couplin agent, 0.5 ml of 200 mg% peroxidase, and 0.1 ml dia lyzed uricase (6 IU/ml) to form a solution containin the composition of the present invention.

The reaction solution so formed was tested by con bining 0.2 ml thereof with 0.01 ml uric acid. The reac tions observed with the various coupling agents whe tested with 5 mg% and 10 mg% concentration uric aci are reported in Table IV.

TABLE IV

| COUPLING AGENT | URIC ACID (mg %) | REACTION OBSERVED |
|---|---|---|
| chromotropic acid | 5 | purple |
| | 10 | purple |
| p-d-methylamino benzaldehyde | 5 | no reaction |
| | 10 | no reaction |
| MBDMA | 5 | pale blue |
| | 10 | pale blue |
| bis (4-hydroxyphenyl) methane | 5 | no reaction |
| | 10 | no reaction |
| primaquine diphosphate | 5 | bright red color |
| | 10 | bright red color |
| iminodibenzyl | 5 | no reaction |
| | 10 | no reaction |

Thus, Table IV shows that chromotropic acid MBDMA and primaquine diphosphate are effectivi when used as coupling agents in the composition of th present invention, whereas certain other compounds namely para-d-methylamino benzaldehyde, bis (4 hydroxyphenyl) methane and iminodibenzyl, are not.

Other compounds which also are effective couplin agents include naphthylethylenediamine, naph thylaminoethanol, hydroxytetrahydrobenzoquinoline phenothiazine, H-acid (8-amino-1-naphthol-6-sulfoni acid), 1-hydroxy-2-napthalenesulfonic acid, 1-hydroxy 3-napthalene-sulfonic acid, 1-amino-2-naphthalene-sul fonic acid, and 6-acetamino-1-hydroxynapthalene-sul fonic acid.

EXAMPLE V

Twenty clear serum samples of unknown uric acic content were anlyzed with devices prepared in a one dip procedure as described below. Results were com pared with test done by the standard phosphotungstat procedure according to Carroll et al., *Clinical Chemis try* 17: 158 (1971).

Ten milliliters (ml) of distilled water containing 0. mg% of 3-methyl-2-benzothiazolinone hydrazon (MBTH), 0.15 mg% peroxidase, 0.075 mg% primaquin diphosphate (PDP), and 1.0 mg% carboxymethylcel lulose were combined with 10 ml of 0.5 Molar (M TRIS at pH 7.0 containing the purified animal inated, uricase-active substance of the present invention having an activity of 3.0 IU/ml.

Sheets of Whatman filter paper 2.54 cm × 10.16 cm in were impregnated with 1 ml each of the above tion, dried for 30 minutes at 50° C., and cut to 5.1 × 10.2 mm to provide devices of the invention. These devices were affixed by double-faced adhesive to elongated polystyrene support member for convenience.

The devices were tested by delivering 0.05 ml of each m sample onto a respective device and reading any or developed after ten seconds and again after five utes. All the readings were generated on an Ames ectance Meter (ARM) (Ames Company, Division Miles Laboratories, Inc., Elkhart, Indiana 46514) a yellow green filter (Edmund Scientific Co., Barton, New Jersey 08007). The difference (Δ) in ARM between the five minutes and ten seconds readings used, to minimize variability in response of handle devices, for comparison with results of testing a sample by the standard phosphotungstate procedure, each of which is stated for the respective samples Table V.

TABLE V

| ample | Ref. Value (mg% uric acid) | ARM units Δ |
|---|---|---|
| 1 | 2.5 | 37 |
| 2 | 3.4 | 41 |
| 3 | 3.5 | 48 |
| 4 | 3.9 | 44 |
| 5 | 4.2 | 49 |
| 6 | 4.3 | 56 |
| 7 | 4.5 | 50 |
| 8 | 4.7 | 57 |
| 9 | 4.8 | 50 |
| 10 | 5.5 | 60 |
| 11 | 5.6 | 59 |
| 12 | 5.6 | 50 |
| 13 | 5.8 | 54 |
| 14 | 6.0 | 70 |
| 15 | 7.0 | 71 |
| 16 | 8.3 | 70 |
| 17 | 8.6 | 91 |
| 18 | 9.0 | 88 |
| 19 | 9.5 | 80 |
| 20 | 10.0 | 86 |

The reading in ARM units varies according to a linear relationship with the concentration in mg% of uric acid present. The result obtained indicated that the tests described correlated to the reference assay procedure were highly sensitive to differences in uric acid el. This sensitivity is evident from the distinct increase in readings between samples varying only htly in uric acid concentration.

EXAMPLE VI

Uric acid test devices were prepared, according to ous formulations in a two-dip procedure as follows. A first dip solution was formed by combining 0.5 ml he dialyzed, uricase-active substance (1.3 IU/ml), in an aqueous solution prepared of 0.1 ml (3.75 mg%) PDP, 0.06 ml (1.5 mg%) peroxidase, and 0.5 ml (1.5 % CMC and 0.8 mg% BRIJ).

A sheet of Whatman filter paper was impregnated to ration with the above first dip solution and dried for ninutes at 60° C. The sheet was then impregnated to ration with 10 ml of 0.05 mg% MBTH in benzene, d for 10 minutes at 60° C., and cut to 5.1 mm × 10.2 to provide devices of the invention.

The devices were tested by delivering 0.03 ml of sample containing uric acid concentrations of 2, 4, 6, 8 and 10 mg% thereto and observing the reflectance after 120 seconds. Readings of 39.3, 34.7, 29.4, 26.9 and 25.8% R were obtained. These readings confirm the inverse relationship defined by the Kubelka-Monk equation referred to earlier and show good sensitivity to the varying concentration of uric acid.

Devices were then made following the above procedure but using PDP concentrations of 1.0, 2.0, and 5.0 mg% instead of 3.75 mg%. Devices so prepared, were tested as above. The %R readings observed at 120 seconds indicated no significant variation in observed sensitivity as a result of the different concentrations of the coupling agent PDP used in the devices.

Likewise, when devices were prepared as described above but using concentrations of the stabilizing agent CMC of 0.5 and 2.4 mg% rather than 1.5 mg%. The devices thus prepared were tested as above and were observed to also detect uric acid with a high level of sensitivity.

Devices were prepared as described above but using the chromogen BMTH at concentrations of 0.01, 0.10 and 0.20 mg% instead of 0.05 mg%. Devices thus prepared were tested as above and likewise demonstrated excellent sensitivity to uric acid concentration.

Devices were prepared as above using peroxidase concentrations of 0.5, 1.0, 5.0 and 20 mg% instead of 1.5 mg%. When tested as above, each device so prepared distinguished uric acid concentrations with the same sensitivity as in the device having 1.5 mg% peroxidase concentration.

Devices were prepared as above using uricase-active substances having activities of 0.8 and 1.8 IU/ml rather than 1.3 IU/ml. When tested as above, no significant variation in sensitivity in the dtection of uric acid was observed as a result of the use of peroxidase of the various indicated activities.

Although the invention has been described with a certain degree of particularity, it is understood that the present disclosure has been made only by way of example and that numerous changes may be resorted to without departing from the spirit and scope of the invention.

What is claimed is:

1. In test means for the detection of uric acid comprising a uricase-active substance, at least one chromogen, and peroxidase, the improvement wherein the uricase-active substance is animal-originated uricase which has been dialyzed against a low metal binding constant buffer, has a pH of from about 6.8 to about 7.5, is stable in said pH range and, is free of pH sensitive contaminants having a molecular weight of less than about 6,000.

2. The test means of claim 1 wherein the chromogen is a hydrazone.

3. The test means of claim 2 wherein the hydrazone is a 3-($C_1$–$C_4$ alkyl)-2-benzothiazolinone hydrazone.

4. The test means of claim 3 wherein the 3-($C_1$–$C_4$ alkyl)-2-benzothiazolinone hydrazone is 3-methyl-2-benzothiazolinone hydrazone.

5. The test means of claim 1 which further comprises at least one coupling agent.

6. The test means of claim 5 wherein said coupling agent is selected from the group consisting of compounds having the general formula:

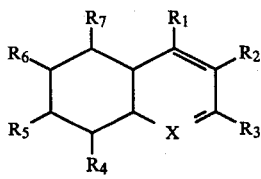

wherein X is C, N, or S; $R_1$ is H, OH, amino, alkylenediamine, or aminoalkanol or combines with $R_2$, where $R_2$ is H, to become $NHCH_2CHOHCH_2$; $R_2$ and $R_3$ are the same or different and are H or $SO_3H$; $R_4$ is H, OH, $NHCH(CH_3)CH_2CH_2CH_2NH_2$, or $SO_3H$; $R_5$ is H, $SO_3H$ or acetamino; $R_6$ is H or $OCH_3$; and $R_7$ is H, OH or $NH_2$; and the acid addition salts, such as the phosphates, thereof: compounds having the general formula $R-CH_2-R$ wherein each R is dimethylaniline, hydroxyphenyl, benzothiazole, or benzophenone: thiamine or its acid addition salt: methylphenylpropanediamine: and phenothiazine.

7. The test means of claim 1 which further comprises at least one stabilizing agent.

8. The test means of claim 7 wherein said stabilizing agent is selected from the group consisting of carboxymethylcellulose and a polyoxyethylene ether of a fatty alcohol.

9. A device for the determination of uric acid in a sample, which device comprises a carrier and, incorporated therewith, the test means of claim 1.

10. The device of claim 9 wherein said carrier is a bibulous or non-bibulous matrix.

11. The device of claim 9 wherein said carrier is a tablet.

12. The method of preparing a purified, animal-originated, uricase active substance, which method comprises dialyzing an animal-originated uri against a buffer having a low metal binding consta a pH of from about 6.8 to about 7.5 to remove pH s tive contaminants having a molecular weight of than about 6,000.

13. A method for producing a device for deterr tion of uric acid in a sample, which method compr
dialyzing an animal-originated uricase to rerr constituents of molecular weight less than 600
preparing a composition containing the thus dialy uricase in combination with 3-($C_1$-$C_4$ alkyl)-2-1 zothiazolinone hydrazone, a coupling agent lected from primaquine diphosphate, chromotr acid, and 4,4'-methylene bis (N,N-dimethyl anil and a peroxidatively active substance; and inco rating a carrier matrix with the composition prepared.

14. The method of claim 13 wherein the step of in porating a carrier matrix with the composition c prises:
impregnating the carrier matrix with a solution o composition; and
drying the matrix so impregnated.

15. A method for determination of uric acid in a s ple, which method comprises:
contacting a sample to be tested with the test m of claim 1, and
observing any resultant color change thereon.

16. A method for determination of uric acid in a s ple, which method comprises:
contacting a sample to be tested with the devic claim 9, and
observing any resultant color change thereon.

* * * * *